United States Patent [19]

Osbon, Sr.

[11] 4,378,008
[45] Mar. 29, 1983

[54] ERECTION AID DEVICE

[76] Inventor: Geddings D. Osbon, Sr., 376 Hill Ave., N. W., Aiken, S.C. 29801

[21] Appl. No.: 264,003

[22] Filed: May 15, 1981

[51] Int. Cl.³ .............................. A61F 5/00
[52] U.S. Cl. .......................... 128/79; 128/303 A
[58] Field of Search ............ 128/79, 303 A, 297–299

[56] References Cited

U.S. PATENT DOCUMENTS

| D. 258,690 | 3/1981 | Wu | 128/79 X |
| 2,874,698 | 2/1959 | Sell | 128/79 |
| 3,744,486 | 7/1973 | Wilson | 128/79 |

FOREIGN PATENT DOCUMENTS

| 313836 | 1/1934 | Italy | 128/299 |
| 347300 | 8/1960 | Switzerland | 128/79 |

Primary Examiner—Dalton L. Truluck
Attorney, Agent, or Firm—Dority & Flint

[57] ABSTRACT

A device for assisting an erection of the male genital organ is disclosed including an evacuation cylinder A having a sealing flange 13 adjacent which a base 14 is carried flush for carrying elastic band 15. Flexible conduit 16 connects to a vacuum source at 18 and a valve 20 is closed to hold a partial vacuum in cylinder A and the organ erect while band 15 is released at just the right time to capture the erection.

3 Claims, 3 Drawing Figures

U.S. Patent  Mar. 29, 1983  4,378,008
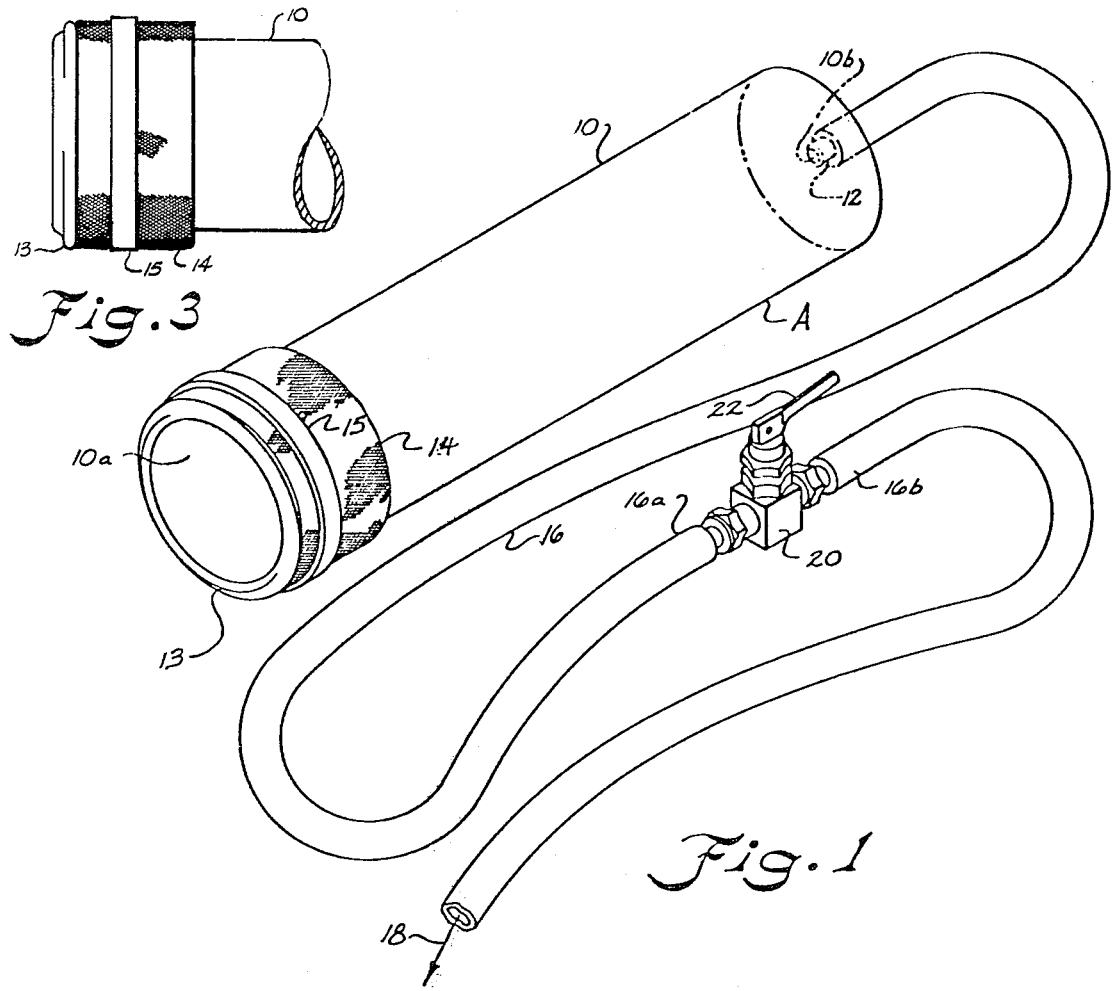
Fig. 3
Fig. 1
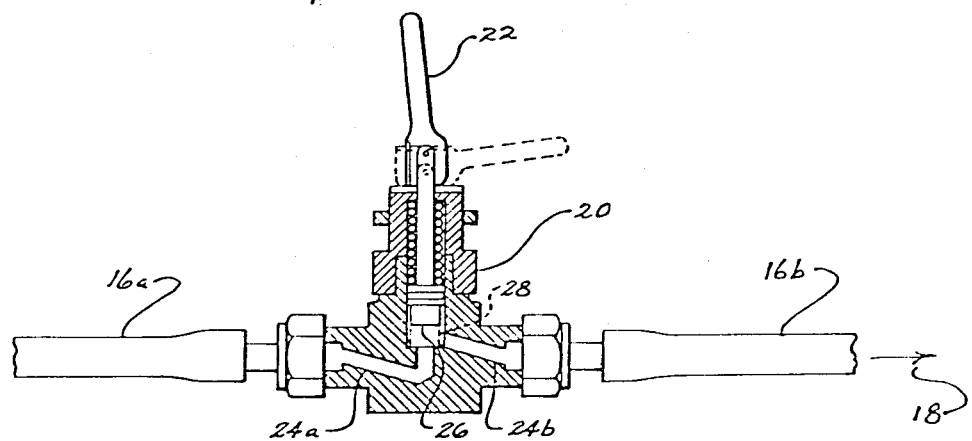
Fig. 2

ERECTION AID DEVICE

BACKGROUND OF THE INVENTION

Heretofore, various devices have been developed to aid in the erection and distention of the male genital organ by inducing blood flow into the organ. These devices have typically included a tube or cylinder that fits about the organ and a pump or similar air evacuating device for creating a partial vacuum in the tube which causes the blood to flow into the organ causing the organ to be erected in a distended configuration such as shown in U.S. Pat. Nos. 3,820,533 and 3,631,853. An elastic band may then be fitted over the base of the organ to restrict the flow of blood out of the organ after removal of the vacuum cylinder to maintain the erection. However, the various devices previously developed for this purpose are partially unsatisfactory because they require unduly complicated arrangements which make utilization awkward and overly artificial. Further, these devices do not allow for carrying out all of the steps involved in the process by means of one simple device.

Accordingly, an important object of the present invention is to provide a device for assisting in the erection of the male genital organ and capturing of that erection which is simple and natural to use.

Yet another object of the present invention is to provide a device for assisting in the erection of the male genital organ in which all of the procedures of erection, and fitting of an elastic band over the base in an erected configuration may be done by means of a single device having a natural and convenient operation.

SUMMARY OF THE INVENTION

The above objectives are accomplished according to the present invention by providing a device which includes an elongated vacuum cylinder which receives the male organ and which is connected by means of a flexible conduit to a vacuum source by which the interior of the cylinder may be evacuated to cause the organ to become erect and distended A manually operated valve is connected in the flexible conduit which may be easily closed to maintain the partial vacuum and organ erect in the cylinder while an elastic band carried adjacent the open end of the cylinder is fitted over the base of the organ whereafter the valve may be opened to relieve the vacuum and remove the vacuum cylinder with the erection being captured.

BRIEF DESCRIPTION OF THE DRAWINGS

The construction designed to carry out the invention will be hereinafter described, together with other features thereof.

The invention will be more readily understood from a reading of the following specification and by reference to the accompanying drawing(s) forming a part thereof, wherein an example of the invention is shown and wherein:

FIG. 1 is a perspective view illustrating a device for assisting in an erection for a male genital organ constructed according to the present invention; and FIG. 2 is a cross-sectional view of the valve and device illustrating the operation of the device of FIG. 1.

FIG. 3 is a partial elevation illustrating a device constructed according to the invention.

DESCRIPTION OF A PREFERRED EMBODIMENT

The invention relates to a device for assisting in the erection and distention of the male organ or penis as a result of increased blood flow into the organ and retaining the organ in this condition.

Referring now in more detail to the drawing, the erection device is illustrated as including an elongated vacuum cylinder A which includes a main tubular portion 10 of adequate dimension to accommodate the organ in a distended configuration which is open at one end 10a and has a reduced opening 10b at the opposing end which terminates in the form of a nipple fitting 12. The open end 10a is defined by a conical or rounded annular shoulder 13 which extends outwardly from the tubular body 10. Shoulder 13 is shaped to form an effective air seal when pressed lightly against the body to provide vacuum more efficiently.

A raised base surface 14 is carried about the tubular body 10 and is contiguous and flush with the annular shoulder 13 so that an elastic band 15 may be carried about the base surface 14 and conveniently pushed off the end and over the annular seat 13 onto a correct position at the base of the organ with cylinder A in place. As illustrated, the base surface 14 is in the form of a semi-rigid sleeve which fits and slides over the tubular body 10 to adjacent the annular shoulder 13, however, it is to be understood that such may also be made as a molded one-piece configuration. The main body portion 10 is preferably transparent so that the condition of the organ may be viewed to insure that a desired erection is obtained prior to releasing band 15.

A flexible conduit 16 is fitted on the nipple fitting 12 of the evacuation cylinder for communicating with a source of vacuum indicated by the arrow 18 by means of which the interior of the vacuum cylinder may be evacuated.

A manually operated valve means 20 is connected in the flexible conduit 16 to define first and second conduit sections 16a and 16b. The manually operated valve may be any conventional two-way valve which may be easily operated when held by one hand. As illustrated, valve 20 has an operator 22 and valve passages 24a and 24b opened and closed by a valve member 26 which is in the form of a spring-loaded quick-release toggle valve, operated by toggle lever 22. The valve has an open position, full line, as shown in FIG. 2 to communicate the interior of the vacuum cylinder with a source of vacuum at arrow 18 so that a desired degree of vacuum may be created in the interior of the vacuum cylinder causing blood to circulate quickly into the penis fitted therein due to the reduced pressure. The blood drawn into the penis lengthens and expands the organ to a distended configuration. Once the desired erection and distention is achieved, the valve is moved to a closed position 28 indicated by the dotted lines of FIG. 2, whereby the vacuum is maintained in the vacuum cylinder A while the elastic band 15 is correctly positioned on the base of the organ to restrict the outflow of blood from the organ. The valve operator 22 is then positioned to open valve member 26 relieving the vacuum enabling the cylinder to be removed. Thus, when the vacuum is relieved in the vacuum cylinder, the erection is maintained.

It is to be understood that any source of vacuum may be utilized and connected to the end of flexible conduit section 16b. However, it has been found that placing the end of the conduit 16b in the mouth and applying a slight sucking action like one sucks on a straw effectively creates desirable vacuum conditions in cylinder A.

The superior principle of the present invention has been found to produce highly satisfactory results achieved by holding the erection in its fully distended state via valve 20 and capturing this erection by releasing the stretched band 15 at just the right time and location from base 14 by means of the simplest manner and device whereafter the valve is opened for relieving vacuum and removal of the device.

The combination of hand valve 20 and flexible vacuum conduit 16 facilitates utilization of the device in a comfortable and natural manner owing to the flexibility and variety of positions during use.

While a preferred embodiment of the invention has been described using specific terms, such description is for illustrative purposes only, and it is to be understood that changes and variations may be made without departing from the spirit or scope of the following claims.

What is claimed is:

1. A device for assisting in an erection of the male genital organ comprising:

an elongated vacuum cylinder including a main tubular portion for accommodating said organ in a distended configuration being open at one end thereof for receiving said organ and having a reduced opening at an opposing end in the form of a nipple fitting;

said receiving end of said vacuum cylinder including an annular contoured shoulder means exending radially outwardly from said tubular portion of said vacuum cylinder forming an air seal with a body portion when held firmly thereagainst;

a raised surface for retaining an elastic band carried about said tubular portion flush and contiguous with said annular shoulder means facilitating reliable removal of said elastic band over said contoured shoulder means for application about said organ simultaneous with removal of said vacuum cylinder from said organ and the breaking of said air seal;

a flexible conduit fitted on said nipple end of said vacuum cylinder for communicating the interior of said vacuum cylinder with a vacuum source to evacuate said cylinder; and a manually-operated valve means connected in said flexible conduit having a closed position to maintain said vacuum in said cylinder and hold the erection while said elastic band is released from said raised surface about said organ at the desired time to capture the erection and an open position for relieving said vacuum once said elastic band is in place for removal of said device.

2. The device of claim 1 wherein said raised surface is provided by a sleeve which is fitted and slidably received upon said tubular portion of said vacuum cylinder.

3. The device of claim 1 wherein said valve means includes a quick-release valve which may be easily and quickly opened and closed.

* * * * *